US012763172B2

(12) United States Patent
Katsuki

(10) Patent No.: US 12,763,172 B2
(45) Date of Patent: Oct. 13, 2026

(54) PREDICTION MODEL FOR DETERMINING WHETHER FEATURE VECTOR OF DATA IN EACH OF MULTIPLE INPUT SEQUENCES SHOULD BE ADDED TO THAT OF THE OTHER DATA IN THE SEQUENCE

(71) Applicant: INTERNATIONAL BUSINESS MACHINES CORPORATION, Armonk, NY (US)

(72) Inventor: Takayuki Katsuki, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1163 days.

(21) Appl. No.: 16/259,706

(22) Filed: Jan. 28, 2019

(65) Prior Publication Data

US 2020/0243165 A1 Jul. 30, 2020

(51) Int. Cl.
*G16C 20/30* (2019.01)
*G06N 7/01* (2023.01)
(Continued)

(52) U.S. Cl.
CPC ............... *G16C 20/30* (2019.02); *G06N 7/01* (2023.01); *G06N 20/00* (2019.01); *G16C 20/70* (2019.02)

(58) Field of Classification Search
CPC ........ G16C 20/30; G16C 20/70; G16C 60/00; G06N 7/005; G06N 20/00; G06N 3/08;
(Continued)

(56) References Cited

U.S. PATENT DOCUMENTS 9,928,468 B2 3/2018 Katsuki et al.
11,087,861 B2 * 8/2021 Takeda .................. G16C 20/20
(Continued)

FOREIGN PATENT DOCUMENTS

CN 108510983 A 9/2018
CN 111489794 A 8/2020
(Continued)

OTHER PUBLICATIONS

Mol2vec: Unsupervised Machine Learning Approach with Chemical Intuition. J. Chem. Inf. Model. 2018, 58, 1, 27-35 Publication Date: Dec. 22, 2017 https://doi.org/10.1021/acs.jcim.7b00616 (Year: 2018).*

(Continued)

*Primary Examiner* — Jennifer N Welch
(74) *Attorney, Agent, or Firm* — CHIP LAW GROUP

(57) ABSTRACT

A method is provided for creating a prediction model that predicts chemical properties of a compound from sequence data as feature vectors describing the compound. The sequence data includes multiple data sequences. The method includes generating a probabilistic prediction model y* for predicting an objective variable y and learned using Bayesian criterion and variational approximation. The method includes configuring the model to (i) assign one of multiple prediction functions for each of the feature vectors extracted from the sequence data, (ii) identify a relationship between a t-th vector in an i-th data and the objective variable y, and (iii) identify similarities of relationships between the feature vectors and the objective variable y. The method includes identifying, using the model, a sequence length which is variable between the multiple data sequences. The method includes predicting the objective variable y as a chemical property of the compound based on the model.

19 Claims, 9 Drawing Sheets

(51) Int. Cl.
*G06N 20/00* (2019.01)
*G16C 20/70* (2019.01)

(58) Field of Classification Search
CPC .......... G06N 3/00; G06N 3/002; G06N 3/004; G06N 3/02; G06N 3/12; G06N 5/00; G06N 5/02; G06N 5/04; G06N 5/01; G06N 7/01; G06N 7/00; G06N 7/02; G06N 7/08
See application file for complete search history.

(56) References Cited

U.S. PATENT DOCUMENTS

| | | | | |
|---|---|---|---|---|
| 2003/0033088 | A1* | 2/2003 | Agrafiotis | G16C 20/10 435/7.1 |
| 2015/0317589 | A1* | 11/2015 | Anderson | G06N 20/20 705/7.25 |
| 2016/0131603 | A1 | 5/2016 | Van Der Mei et al. | |
| 2017/0193200 | A1 | 7/2017 | Hsu et al. | |
| 2017/0200265 | A1* | 7/2017 | Bhaskar | G03F 1/86 |
| 2018/0071425 | A1* | 3/2018 | Jin | A61L 9/14 |
| 2018/0336486 | A1 | 11/2018 | Chu et al. | |
| 2019/0172584 | A1* | 6/2019 | Athey | A61K 31/37 |
| 2019/0261565 | A1* | 8/2019 | Robertson | B25J 11/00 |
| 2019/0286791 | A1* | 9/2019 | Takeda | G16C 20/30 |
| 2025/0292157 | A1* | 9/2025 | Oono | G06N 20/00 |

FOREIGN PATENT DOCUMENTS

| | | |
|---|---|---|
| EP | 1 525 534 | 3/2016 |
| WO | 2007023903 A | 3/2007 |

OTHER PUBLICATIONS

Huang Y, Tienda-Luna IM, Wang Y. A Survey of Statistical Models for Reverse Engineering Gene Regulatory Networks. IEEE Signal Process Mag. 2009;26(1):76-97. doi:10.1109/MSP.2008.930647 (Year: 2009).*

Phoenics: A Bayesian Optimizer for Chemistry, Haseetal, ACSCentSci. 41134-1145 (Year: 2018).*

Automatic Chemical Design Using a Data-Driven Continuous RepresentationofMolecules, RafaelGomez-Bombarelli,ACDCentSci,4. 268-176. (Year: 2018).*

Constrained Bayesian Optimization for Automatic Chemical Design. Griffiths.Sep. 2017 (Year: 2017).*

Mol2vec: Unsupervised Machine Learning ApproachwithChemicalIntuition.J.Chem.Inf.Model.2018,58,1,27-35 Publication Date:Dec. 22,2017 httos://doi.org/10.1021/acs.jcim.7600616 (Year: 2018).*

Rafael Gomez-Bombarelli et al., Automatic Chemical Design Using a Data-Driven Continuous Representation of Molecules, Jan. 12, 2018, ACS Cent. Sci. 2018, 4, 268-276 (Year: 2018).*

Kang et al., Conditional Molecular Design with Deep Generative Models, 2018 (Year: 2018).*

Huang et al Adversarial Machine Learning *InProceedingsof4thACMWorkshoponArtificialIntelligenceandSecurity, Oct. 2011, pp. 43-58 (Year: 2011).*

HuangY, Tienda-LunaIM, WangY. A Survey of Statistical Mode Is for Reverse Engineering Gene Regulatory Networks. IEEE Signal Process Mag. 2009;26(1):76-97.doi:10.1109/MSP.2008.930647 (Year: 2009).*

Gao et al., "Using Machine Learning To Predict Suitable Conditions for Organic Reactions", 2018, ACS Central Science, vol. 4 No. 11, pp. 1465-1476 (Year: 2018).*

Varnek et al., "Machine Learning Methods for Property Prediction in Chemoinformatics: Quo Vadis?", 2012, Journal of Chemical Information and Modeling (Year: 2012).*

Ikebata et al, "Bayesian molecular design with a chemical language model", J Comput Aided Mol Des, 2017, pp. 379-391.*

Katsuki et al., "Bayesian Regression Selecting Valuable Subset from Mixed Bag Training Data", 2016 23rd International Conference on Pattern Recognition (ICPR), Dec. 2016, pp. 2581-2586.

Hu, W., & Wang, H. (Apr. 30, 2010). Prediction modeling based on Bayes support vector machine. Journal of Beijing University of Aeronautics and Astronautics, 36(4), 486.

Li, B. K., Cong, Y., Tian, Z. Y., & Xue, Y. (Jan. 15, 2014). Predicting and virtually screening the selective Inhibitors of mmp-13 over mmp-1 by molecular descriptors and machine learning methods. Acta Physico-Chimica Sinica, 30(1), 171-182.

Office Action from CN202010040634.5 dated Nov. 7, 2023. (6 pages).

* cited by examiner

PREDICTION MODEL FOR DETERMINING WHETHER FEATURE VECTOR OF DATA IN EACH OF MULTIPLE INPUT SEQUENCES SHOULD BE ADDED TO THAT OF THE OTHER DATA IN THE SEQUENCE

BACKGROUND

Technical Field

The present invention generally relates to prediction modeling, and more particularly to a prediction model for determining whether a feature vector of data in each of multiple input sequences should be added to that of the other data in the sequence.

Description of the Related Art

Predicting chemical properties (e.g., but not limited to, glass transition temperature, viscosity, etc.) of a compound material from its compounding process ("reaction recipe" or "recipe" in short) is an important task for various chemical as well as other industries. The recipes (chemical compounding processes) are the sequences of the quantity of ingredients. A model is constructed to predict the chemical properties of a compound material.

However, a problem exists in that a corresponding prediction model has to be learned that can have the following input and output relation by using pairs of input and a corresponding output, where the input includes sequence data (a set of T numbers of V-dimensional vectors), the output includes a prediction model of the objective variable from the sequential data (that is, a scalar, e.g., a chemical property), and assumptions are made such as all vectors in the sequence are important for the prediction but are often verbose and vague. Further assumptions can include: (1) the relationship between t-th vector in the i-th data and objective variable and that between t-th vector in the I'-th data and objective variable may be different; (2) the relationship between t-th vector in the i-th data and objective variable and that between t'-th vector in the I'-th data and objective variable may be same; (3) the length of each sequence is different; (4) the t-th vector and t+1-th vector may have a similar relationship to an objective function; (5) a requirement to obtain knowledge about the role of t-th vector for each data from the prediction model; and (6) the number of labeled training data is limited in many real-world problems (e.g., the number of existing materials in a certain category is not so large). For example, we want to classify the ingredients based on their nature (e.g., base ingredient or additive ingredient) to assign a different prediction function, which is different for each i-th data. The length of the sequence is different for each i-th data. Handling them may be trivial for domain experts but not for a data analyst or in some cases we can only obtain feature vectors or code without the information such as the original chemical formulas.

In sequential data analysis, it is required to summarize redundant parts of the sequence properly for each data sample, but there are no established general methods for extracting a feature vector from sequential data in consideration of that.

Hence, there is a need for a prediction model that can determine whether the feature vector of the data in each of multiple input data sequences should be added to that of the other ones of the multiple input data sequences.

SUMMARY

According to an aspect of the present invention, a computer-implemented method is provided for creating a prediction model that predicts chemical properties of a compound from sequence data as a set of feature vectors describing the compound. The sequence data includes multiple data sequences. The method includes generating, by a hardware processor, a probabilistic prediction model y* for predicting an objective variable y and learned using Bayesian criterion and variational approximation. The method further includes configuring, by the hardware processor, the probabilistic prediction model y* to (i) assign one of multiple prediction functions for each of the feature vectors extracted from the sequence data, (ii) identify a relationship between a t-th vector in an i-th data and the objective variable y, and (iii) identify similarities of relationships between the feature vectors and the objective variable y. The method also includes identifying, by the hardware processor using the probabilistic prediction model y*, a sequence length which is variable between the multiple data sequences. The method further includes predicting, by the hardware processor, the objective variable y as a chemical property of the compound based on the probabilistic prediction model y*.

According to another aspect of the present invention, a computer program product is provided for predicting properties of an object from sequence data describing the object. The computer program product includes a non-transitory computer readable storage medium having program instructions embodied therewith. The program instructions are executable by a computer to cause the computer to perform a method. The method includes generating, by a hardware processor, a probabilistic prediction model y* for predicting an objective variable y and learned using Bayesian criterion and variational approximation. The method further includes configuring, by the hardware processor, the probabilistic prediction model y* to (i) assign one of multiple prediction functions for each of the feature vectors extracted from the sequence data and (ii) identify a relationship between a t-th feature vector in an i-th data and the objective variable y, and (iii) identify similarities of relationships between the feature vectors and the objective variable y. The method also includes identifying, by the hardware processor using the probabilistic prediction model y*, a sequence length which is variable between the multiple data sequences. The method additionally includes predicting, by the hardware processor, the objective variable y as a chemical property of the compound based on the probabilistic prediction model y*.

According to yet another aspect of the present invention, a computer processing system is provided for predicting properties of an object from sequence data describing the object. The computer processing system includes a memory for storing program code. The computer processing system further includes a hardware processor for executing the program code to generate a probabilistic prediction model y* for predicting an objective variable y and learned using Bayesian criterion and variational approximation. The hardware processor further executes the program code to configure the probabilistic prediction model y* to (i) assign one of multiple prediction functions for each of the feature vectors extracted from the sequence data and (ii) identify a relationship between a t-th feature vector in an i-th data and the objective variable y, and (iii) identify similarities of relationships between the feature vectors and the objective variable y. The processor also executes the program code to identify, using the probabilistic prediction model y*, a sequence length which is variable between the multiple data sequences. The processor additionally executes the program code to predict the objective variable y as a chemical property of the compound based on the probabilistic prediction model y*.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

The present invention is directed to a prediction model for determining whether a feature vector of data in each of multiple input sequences should be added to that of the other data in the sequence.

In an embodiment, the present invention involves assigning one of the small number of the shared prediction functions to the t-th vector for each i-th data and predicting the objective variable by the summation of the outputs of the small number of shared prediction functions.

Hence, compared to Multiple Instance Regression, the present invention can use all the vectors in the i-th data by assigning a different prediction function to each of them.

Moreover, compared to a nonlinear prediction model, the present invention can accept the different sequence lengths and reduce the number of required parameters as well as reduce the required number of training data.

Further, compared to a time-series model, the present invention can reduce the number of required parameters as well as reduce the required number of training data, because the proposed model can share the prediction functions.

From the assigned functions, the present invention can interpret the group of role of the vector.

Figure 1:
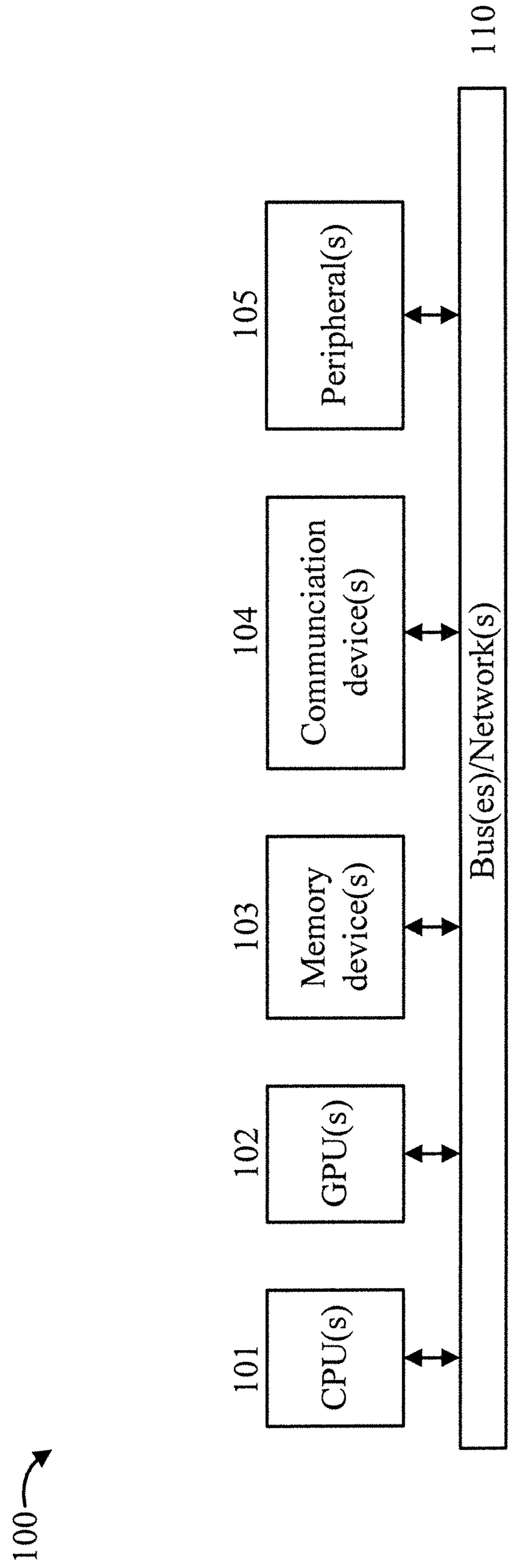
FIG. 1 is a block diagram showing an exemplary processing system to which the present invention may be applied, in accordance with an embodiment of the present invention.

FIG. 1 is a block diagram showing an exemplary processing system 100 to which the present invention may be applied, in accordance with an embodiment of the present invention. The processing system 100 includes a set of processing units (e.g., CPUs) 101, a set of GPUs 102, a set of memory devices 103, a set of communication devices 104, and set of peripherals 105. The CPUs 101 can be single or multi-core CPUs. The GPUs 102 can be single or multi-core GPUs. The one or more memory devices 103 can include caches, RAMs, ROMs, and other memories (flash, optical, magnetic, etc.). The communication devices 104 can include wireless and/or wired communication devices (e.g., network (e.g., WIFI, etc.) adapters, etc.). The peripherals 105 can include a display device, a user input device, a printer, an imaging device, and so forth. Elements of processing system 100 are connected by one or more buses or networks (collectively denoted by the figure reference numeral 110).

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. Further, in another embodiment, a cloud configuration can be used (e.g., see FIGS. 7-8). These and other variations of the processing system 100 are readily contemplated by one of ordinary skill in the art given the teachings of the present invention provided herein.

Moreover, it is to be appreciated that various figures as described below with respect to various elements and steps relating to the present invention that may be implemented, in whole or in part, by one or more of the elements of system 100.

A description will now be given regarding six aspects of the present invention, as described with respect to six cases relating to various embodiments of the present invention. These cases can be implemented in any combination, including one, some, and up to all, as readily appreciated by one of ordinary skill in the art given the teachings of the present invention provided herein, while maintaining the spirit of the present invention. Thereafter, a method is described relative to FIG. 2 in order to provide an overview of a method in accordance with the present invention. Another method is described relative to FIGS. 3-4 in order to provide a further detailed method relative to the method described in relation to FIG. 2.

As noted above, the present invention is directed to generating a prediction model which can determine whether the feature vector of the data in each of multiple input data sequences should be added to that of other data in the other input data sequences. In this way, the present invention can be used to predict chemical properties of a compound material from its compounding process, as well as prediction of other properties of an item from a data sequence relating to the item.

To that end, in an embodiment (case 1), a prediction model is learned which assigns one of a small number (e.g., smaller than T or N) of prediction functions for each feature vector in each i-th data and uses the summation of the outputs of the (assigned) prediction functions as its prediction. For example, in an embodiment, a dataset having the following input and output relationship can be used: input=sequence data (set of T numbers of V-dimensional feature vectors; output=object variable (scalar, e.g., a chemical (or other) property).

In an embodiment (case 2), a prediction function is assigned by the estimation of a hidden variable $\eta$ which explicitly represents the assignation of the function. $\eta_{i,t,d}$ in $\eta_i$ is a binary variable representing assigning the d-th function to the t-th vector in the i-th data $\Sigma_d\ \eta_{i,t,d}=1$. This estimation result represents the roles of the feature vectors in each i-th data.

In an embodiment (case 3), for objective variable y and t-th vector $x_t$ in X, we assume the following probabilistic model, and learn the parameters using the training data to conduct case 1.

$$p\left(y \mid X, \{w_d\}_{d=0}^{D}, \beta, \{\eta_t\}_{t=0}^{T}\right) = \text{Gauss}\left(y \mid \sum\nolimits_d \sum\nolimits_t w_d \eta_{t,d} x_t, 1/\beta\right)$$

$$p\left(x_t \mid \{w_d\}_{d=0}^{D}, \{\xi_d\}_{d=0}^{D}, \eta_t\right) = \sum_d \text{Gauss}(x_t \mid u_d, 1/\xi_d)^{\eta_{t,d}}$$

where

X is a set of input sequences in training data, y is an objective variable in the training data, w, β, μ, ξ are parameters to be learned The nonlinear function for the mean of y can be used The mixture component of the probabilistic model for $x_t$ can be replaced with neural networks.

In an embodiment (case 4), assume the following probabilistic distribution for the hidden variable $\eta$:

$$p(\eta_t \mid \eta_{t-1}, k_{t,t-1}, \lambda_{t,d}) = \exp\left(-k_{t,t-1}\left(1 - \eta_t^T \eta_{t-1}\right) - \sum_d \lambda_{t,d}(1 - \eta_{t,d})\right)$$

where k, λ are parameters to be learned.

Other relationships using different forms of the distribution (e.g., t-th vector is related to all other vectors in i-th data) can be used.

In an embodiment (case 5), the following probabilistic prediction model y* for predicting objective variable y which is learned using Bayesian criterion can be used:

$$y^*\left(X, Y, \{X_i\}_{i=1}^{N}\right) = \text{argmin}_{y^*} \int p\left(y, X, Y, \{X_i\}_{i=1}^{N}, \theta\right)(y^* - y)^2 dy\, dX\, dY\, d\{X_i\}_{i=1}^{N} d\theta = \int p\left(y \mid X, Y, \{X_i\}_{i=1}^{N}\right) y\, dy$$

where $$Y = \{y_i\}_{i=1}^{N}$$

is the set of objective variables in the training data, $$\{X_i\}_{i=1}^{N}$$

is the set of input sequences in the training data,

θ is the set of parameters to be learned, p(w)=Automatic Relevance Determination (ARD) (Bayesian sparse learning), and p(β, ξ, κ, λ)→independent Gamma distributions (to restrict the parameters to positive values).

In an embodiment (case 6), the equation in case 5 is solved with variational approximation.

Figure 2:
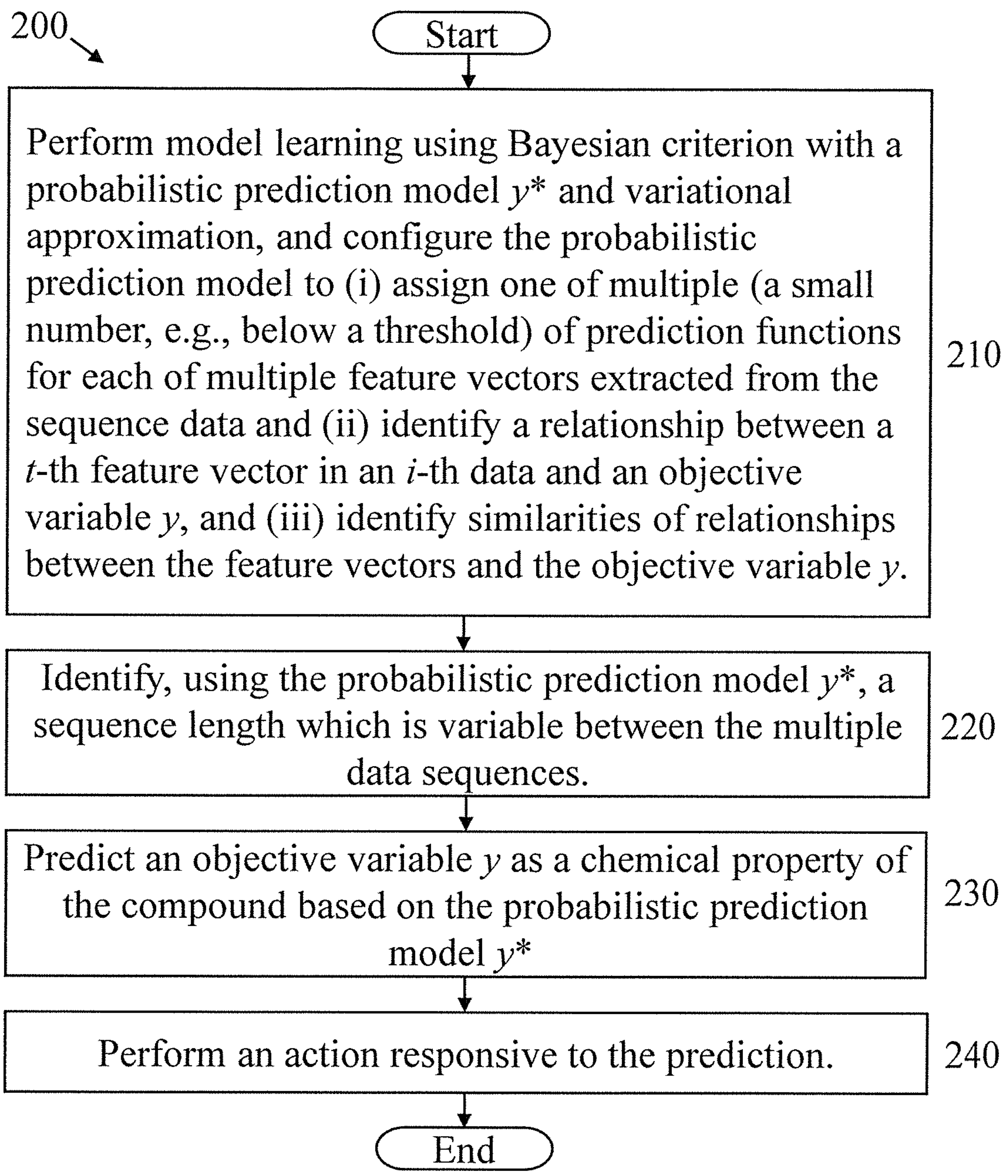
FIG. 2 is a flow diagram showing an exemplary method for generating a prediction model, in accordance with an embodiment of the present invention.

FIG. 2 is a flow diagram showing an exemplary method 200 for generating a prediction model, in accordance with an embodiment of the present invention.

At block 210, perform model learning using Bayesian criterion with a probabilistic prediction model y* and variational approximation, and configure the probabilistic prediction model to (i) assign one of multiple (a small number, e.g., below a threshold) of prediction functions for each of multiple feature vectors extracted from the sequence data and (ii) identify a relationship between a t-th feature vector in an i-th data and an objective variable y, and (iii) identify similarities of relationships between the feature vectors and the objective variable y.

At block 220, identify, using the probabilistic prediction model y*, a sequence length which is variable between the multiple data sequences.

At block 230, predict an objective variable y as a chemical property of the compound based on the probabilistic prediction model y*.

At block 240, perform an action responsive to the prediction. Exemplary actions are described below with respect to FIGS. 5 and 6.

Figure 3:
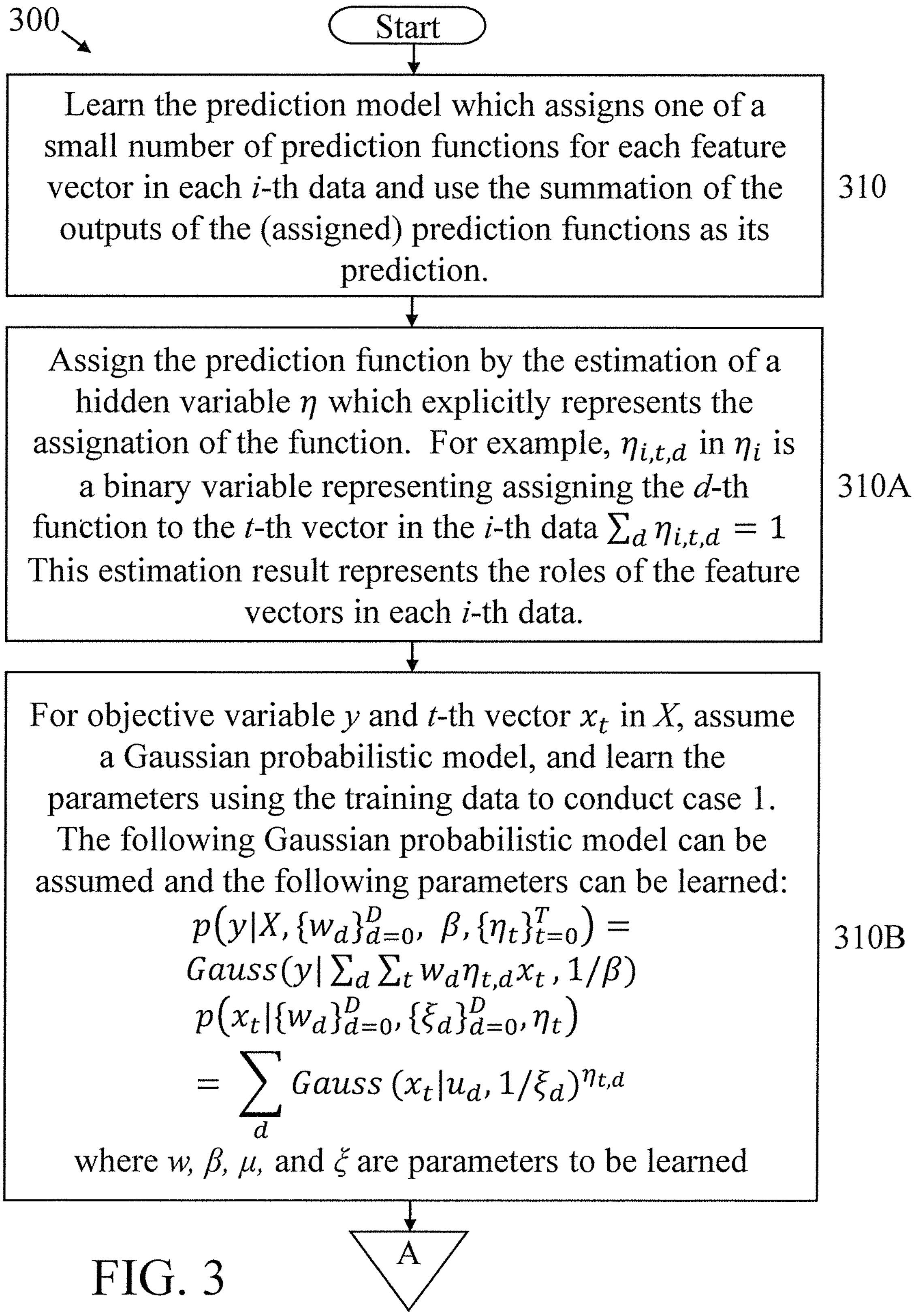
FIGS. 3-5 are flow diagrams showing another exemplary method for generating a prediction model, in accordance with an embodiment of the present invention.
Figure 4:
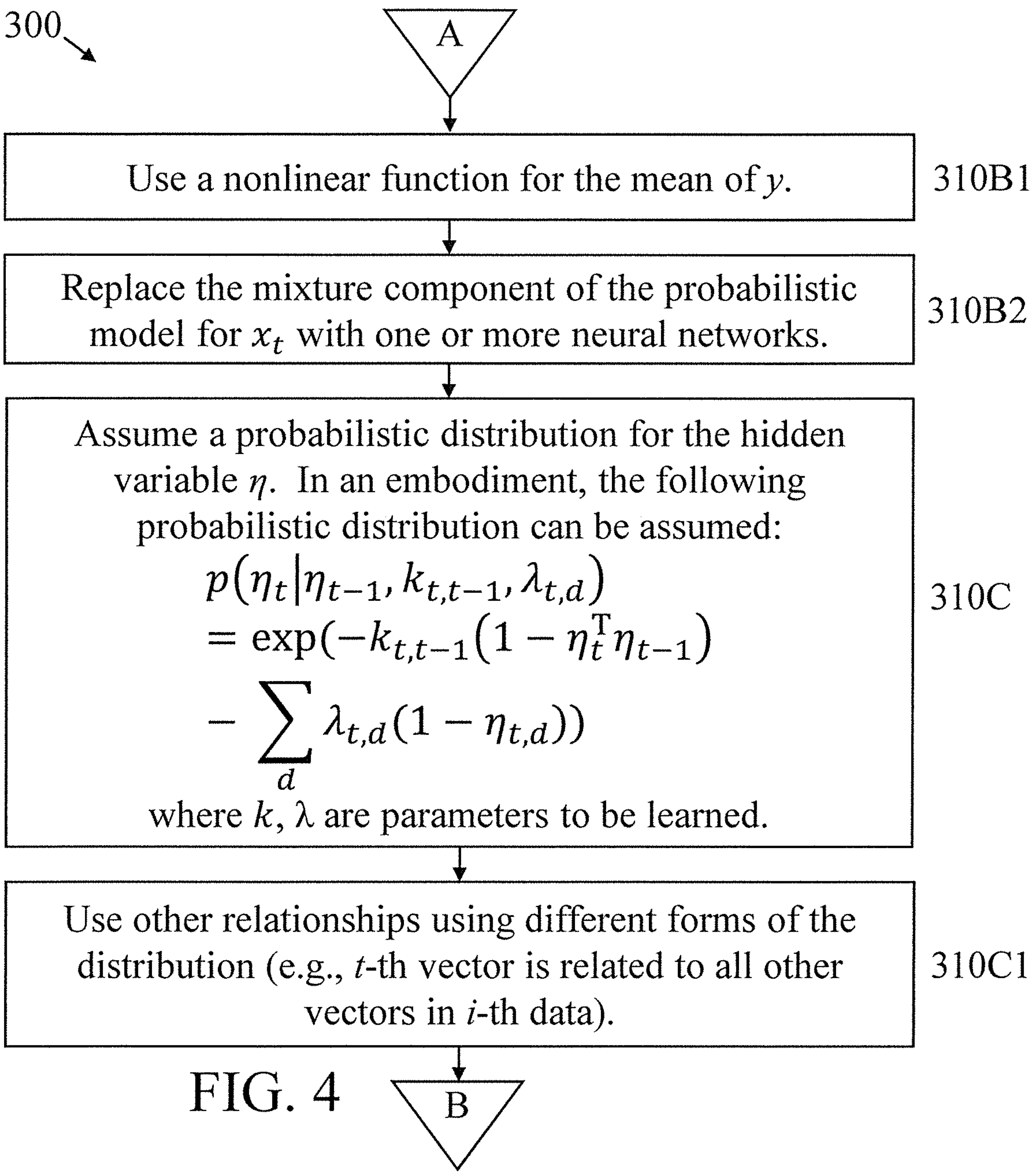
Figure 5:
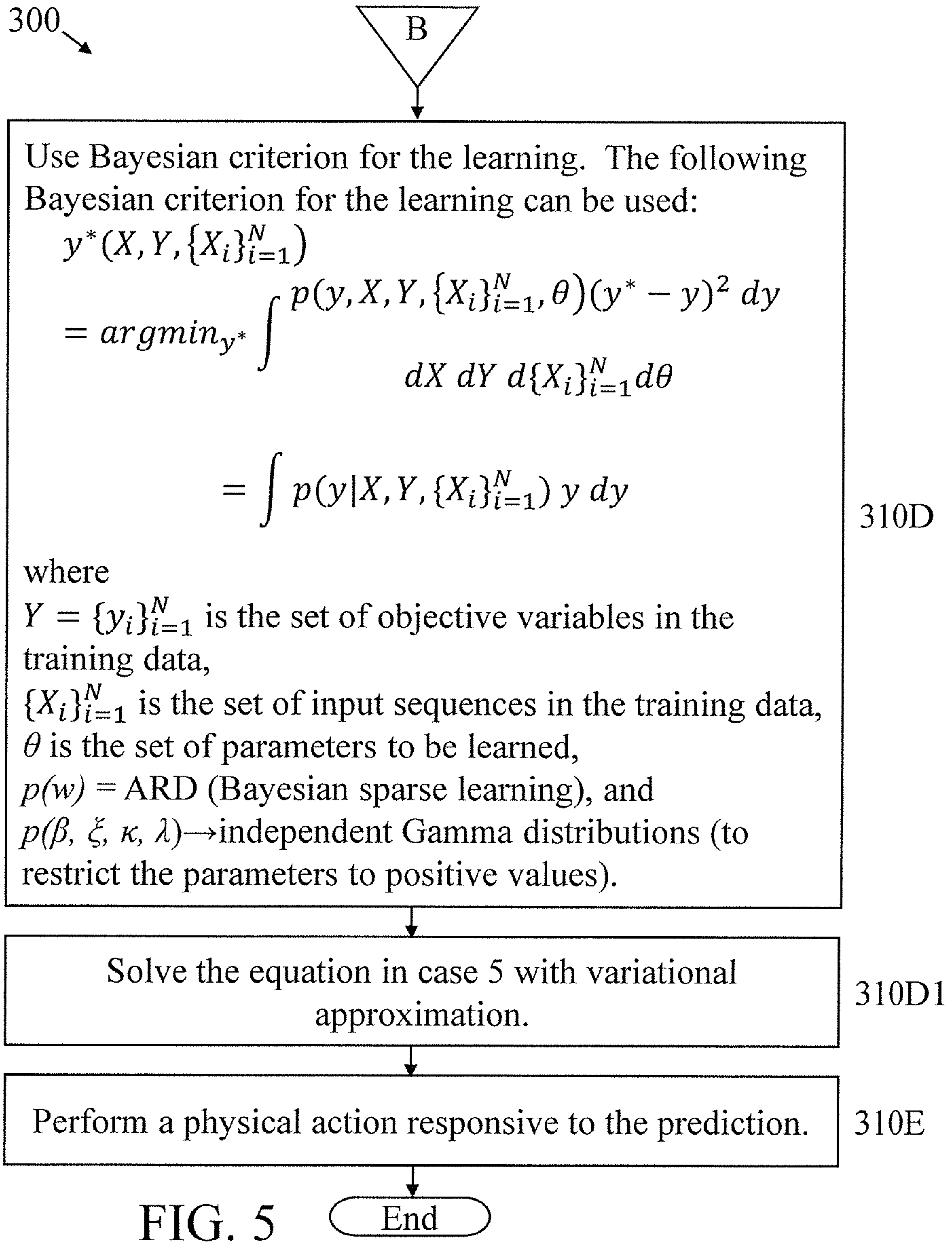

FIGS. 3-5 are flow diagrams showing another exemplary method 300 for generating a prediction model, in accordance with an embodiment of the present invention. The prediction model is generated to be able to predict (determine) whether the feature vector of the data in each of multiple input data sequences should be added to that of other data in the other input data sequences.

At block 310 (case 1), learn the prediction model which assigns one of a small number of prediction functions for each feature vector in each i-th data and use the summation of the outputs of the (assigned) prediction functions as its prediction.

In an embodiment, block 310 can include one or more of blocks 310A-310X.

At block 310A (case 2), assign the prediction function by the estimation of a hidden variable $\eta$ which explicitly represents the assignation of the function. For example, $\eta_{i,t,d}$ in $\eta_i$ is a binary variable representing assigning the d-th function to the t-th vector in the i-th data $\Sigma_d \eta_{i,t,d}=1$. This estimation result represents the roles of the feature vectors in each i-th data.

At block 310B (case 3), for objective variable y and t-th vector $x_t$ in X, assume a Gaussian probabilistic model, and learn the parameters using the training data to conduct case 1. In an embodiment, the following Gaussian probabilistic model can be assumed and the following parameters can be learned:

$$p\left(y \mid X, \{w_d\}_{d=0}^{D}, \beta, \{\eta_t\}_{t=0}^{T}\right) = \text{Gauss}\left(y \mid \sum\nolimits_d \sum\nolimits_t w_d \eta_{t,d} x_t, 1/\beta\right)$$

$$p\left(x_t \mid \{w_d\}_{d=0}^{D}, \{\xi_d\}_{d=0}^{D}, \eta_t\right) = \sum_d \text{Gauss}(x_t \mid u_d, 1/\xi_d)^{\eta_{t,d}}$$

where

X is a set of input sequences in training data, y is an objective variable in the training data, w, β, μ, and ξ are parameters to be learned, such that w represents a weight vector for the features, β represents a precision parameter of the Gaussian distribution, and μ represents prior mean parameters in the Gaussian mixture for the prior distribution for x.

In an embodiment, block 310B includes one or more of blocks 310B1 and 310B2.

At block 310B1 (case 3), use a nonlinear function for the mean of y.

At block 310B2 (case 3), replace the mixture component of the probabilistic model for $x_t$ with one or more neural networks.

At block 310C (case 4), assume a probabilistic distribution for the hidden variable η. In an embodiment, the following probabilistic distribution can be assumed:

$$p(\eta_t \mid \eta_{t-1}, k_{t,t-1}, \lambda_{t,d}) = \exp\left(-k_{t,t-1}\left(1-\eta_t^T\eta_{t-1}\right) - \sum_d \lambda_{t,d}(1-\eta_{t,d})\right)$$

where k and λ are parameters to be learned such that k represents a strength of co-occurrence of the same prediction function in the t-th and t−1-th vectors, and λ represents a strength of selecting the d-th component $$p\left(x_t \middle| \{w_d\}_{d=0}^D, \{\xi_d\}_{d=0}^D, \eta_t\right)$$

for t-th vector.

In an embodiment, block 310C can include block 310C1.

In block 310C 1, use other relationships using different forms of the distribution (e.g., t-th vector is related to all other vectors in i-th data).

At block 310D (case 5), use Bayesian criterion for the learning. In an embodiment, the following Bayesian criterion for the learning can be used:

$$y^*\left(X, Y, \{X_i\}_{i=1}^N\right) = \mathrm{argmin}_{y^*} \int p\left(y, X, Y, \{X_i\}_{i=1}^N, \theta\right)(y^*-y)^2 dy\, dX\, dY\, d\{X_i\}_{i=1}^N d\theta = \int p\left(y \mid X, Y, \{X_i\}_{i=1}^N\right) y\, dy$$

where $$Y = \{y_i\}_{i=1}^N$$

is the set of objective variables in the training data, $$\{X_i\}_{i=1}^N$$

is the set of input sequences in the training data,

θ is the set of parameters to be learned, p(w)=ARD (Bayesian sparse learning), and p(β, ξ, κ, λ)→independent Gamma distributions (to restrict the parameters to positive values).

In an embodiment, block 310D can include block 310D1.

At block 310D1 (case 6), solve the equation in case 5 (block 310D) with variational approximation.

At block 310E, perform an action responsive to the prediction.

A description will now be given regarding two exemplary environments 600 and 700 to which the present invention can be applied, in accordance with various embodiments of the present invention. The environments 600 and 700 are described below with respect to FIGS. 6 and 7, respectively. In further detail, the environment 600 includes a prediction system operatively coupled to a controlled system, while the environment 700 includes a prediction system as part of a controlled system. Moreover, any of environments 600 and 700 can be part of a cloud-based environment (e.g., see FIGS. 8 and 9). These and other environments to which the present invention can be applied are readily determined by one of ordinary skill in the art, given the teachings of the present invention provided herein, while maintaining the spirit of the present invention.

Figure 6:
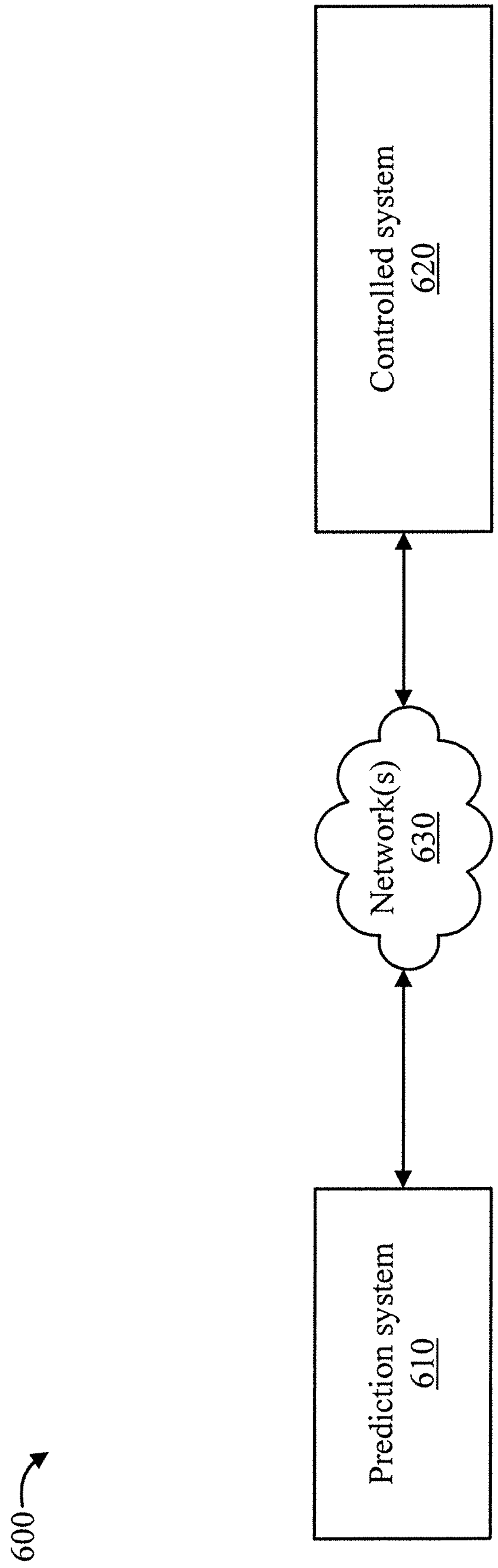
FIG. 6 is a block diagram showing an exemplary environment to which the present invention can be applied, in accordance with an embodiment of the present invention.

FIG. 6 is a block diagram showing an exemplary environment 600 to which the present invention can be applied, in accordance with an embodiment of the present invention.

The environment 600 includes a prediction system 610 and a controlled system 620. The prediction system 610 and the controlled system 620 are configured to enable communications therebetween. For example, transceivers and/or other types of communication devices including wireless, wired, and combinations thereof can be used. In an embodiment, communication between the prediction system 610 and the controlled system 620 can be performed over one or more networks, collectively denoted by the figure reference numeral 630. The communication can include, but is not limited to, sequence data from the controlled system 620, and predictions and action initiation control signals from the prediction system 610. The controlled system 620 can be any type of processor-based system such as, for example, but not limited to, a banking system, an access system, a surveillance system, a manufacturing system (e.g., an assembly line), an Advanced Driver-Assistance System (ADAS), and so forth.

The controlled system 620 provides data (e.g., sequence data) to the prediction system 610 which uses the data to make predictions.

The controlled system 620 can be controlled based on a prediction generated by the prediction system 610. For example, the controlled system can be a manufacturing system that manufactures a given item (food, fragrance, medicine to treat diseases/conditions, etc.) using a compounding process (reaction recipe). Based on a prediction that a compound is contaminated (includes a component/element that it should not include) or does not include the required and/or expected amounts of the constituent elements, the resultant compound can be discarded or its recipe altered and new batches made to prevent future contamination or to provide the required and/or expected amounts of constituent elements forming a compound. Thus, the present invention can apply for predictions where too much or too little or none of an element is included in a compound as well as predictions where an unexpected element is present. As another example, based on what is expected to be seen by a surveillance system as normal, an out-of-place object can be detected as such and an action (e.g., place the object in a bomb-disposal container to mitigate a potential resultant blast, etc.) performed with respect to the out-of-place object. As a further example, a vehicle can be controlled (braking, steering, accelerating, and so forth) to avoid an obstacle that is predicted to be in a car's way responsive to a prediction that includes something is in the way of the vehicle that shouldn't be (a pedestrian, animal, tree branch, etc.). Basically, the present invention can be used for any application where it is desired to know the constituent elements of a compound. Hence, it is to be appreciated that the preceding actions are merely illustrative and, thus, other actions can also be performed depending upon the implementation, as readily appreciated by one of ordinary skill in the art given the teachings of the present invention provided herein, while maintaining the spirit of the present invention.

In an embodiment, the prediction system 610 can be implemented as a node in a cloud-computing arrangement. In an embodiment, a single prediction system 610 can be assigned to a single controlled system or to multiple controlled systems e.g., different robots in an assembly line, and so forth). These and other configurations of the elements of environment 600 are readily determined by one of ordinary skill in the art given the teachings of the present invention provided herein, while maintaining the spirit of the present invention.

Figure 7:
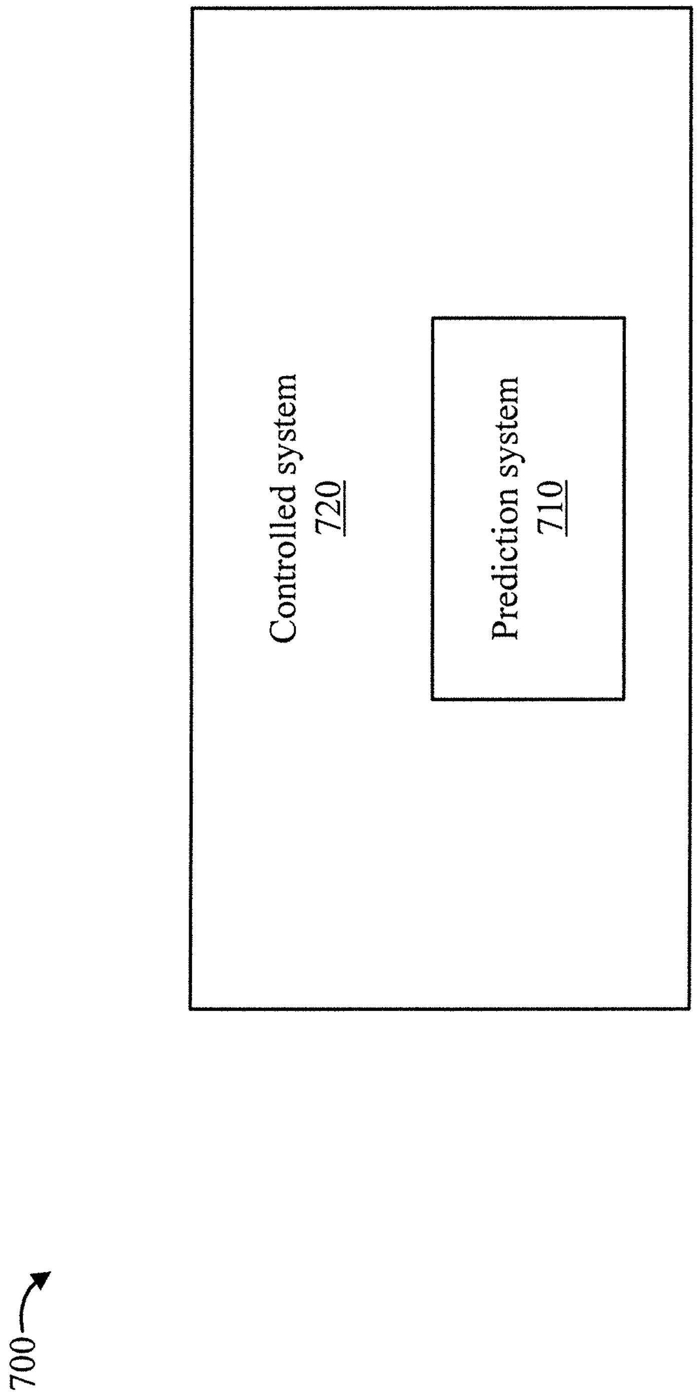
FIG. 7 is a block diagram showing another exemplary environment to which the present invention can be applied, in accordance with an embodiment of the present invention.

FIG. 7 is a block diagram showing another exemplary environment 700 to which the present invention can be applied, in accordance with an embodiment of the present invention.

The environment 700 includes a controlled system 720 that, in turn, includes a prediction system 710. One or more communication buses and/or other devices can be used to facilitate inter-system, as well as intra-system, communication. The controlled system 720 can be any type of processor-based system such as, for example, but not limited to, a banking system, an access system, a surveillance system, a manufacturing system (e.g., an assembly line), an Advanced Driver-Assistance System (ADAS), and so forth.

Other than system 710 being included in system 720, operations of these elements in environments 700 and 700 are similar. Accordingly, elements 710 and 720 are not described in further detail relative to FIG. 7 for the sake of brevity, with the reader respectively directed to the descriptions of elements 710 and 720 relative to environment 600 of FIG. 7 given the common functions of these elements in the two environments 600 and 700.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
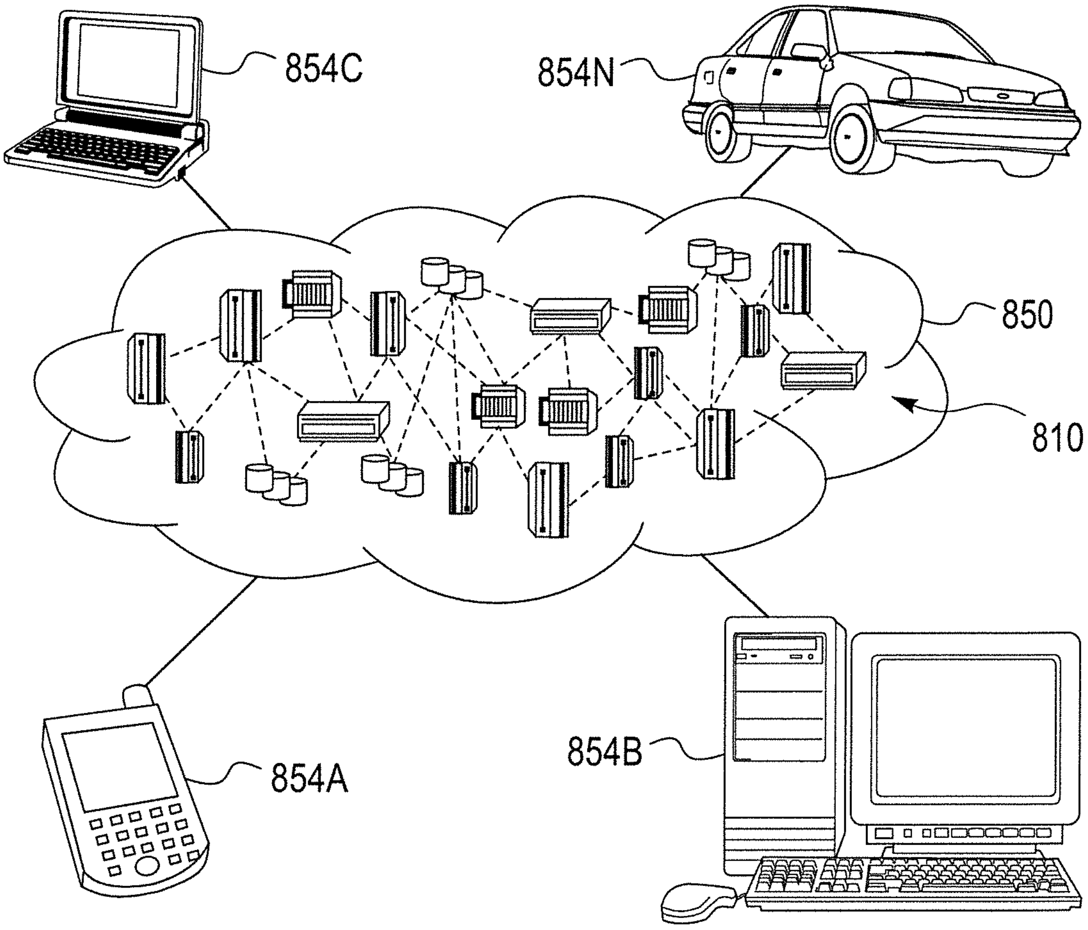
FIG. 8 is a block diagram showing an illustrative cloud computing environment having one or more cloud computing nodes with which local computing devices used by cloud consumers communicate, in accordance with an embodiment of the present invention.

Referring now to FIG. 8, illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Nodes 810 may communicate with one another. They may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
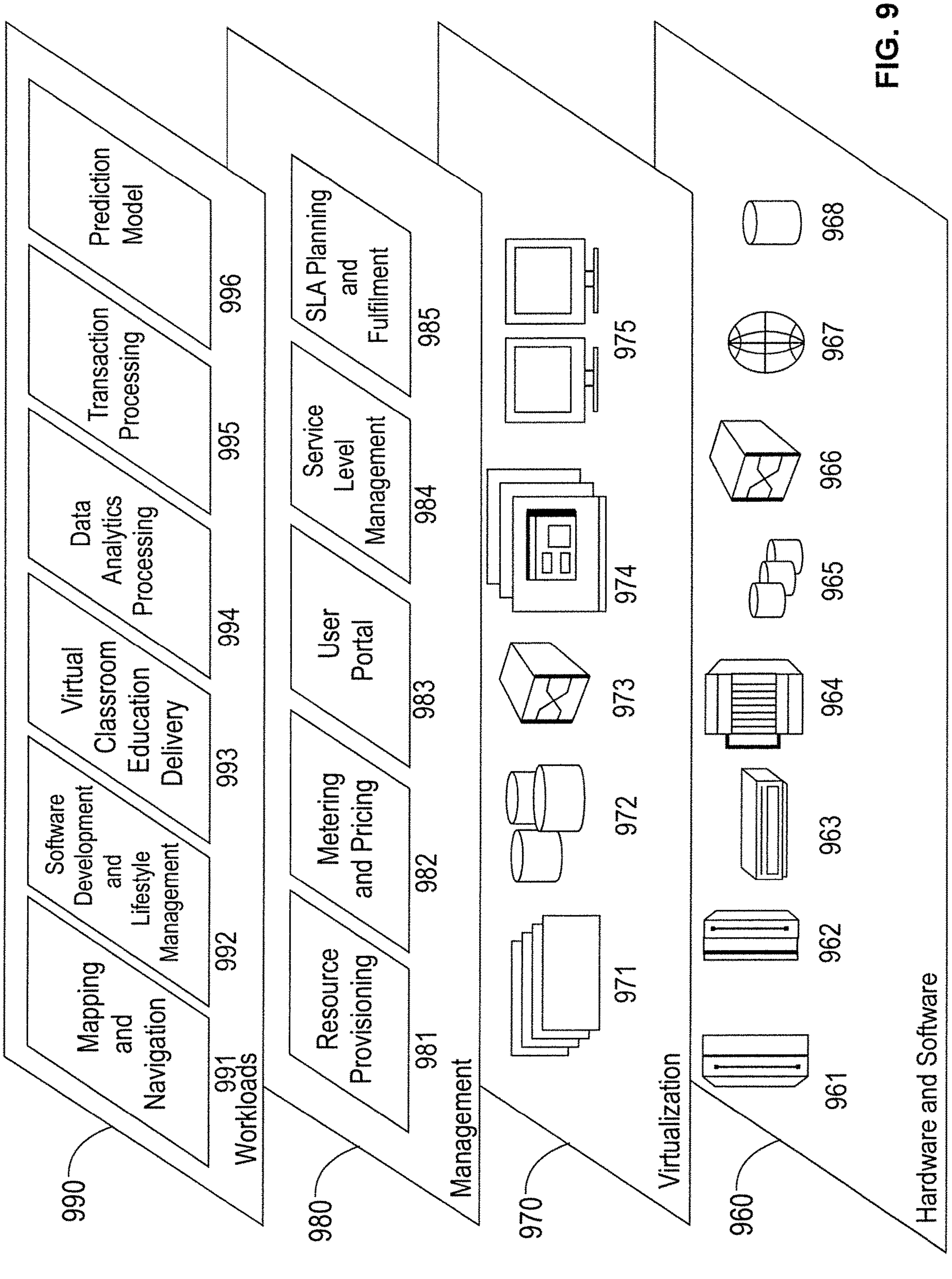
FIG. 9 is a block diagram showing a set of functional abstraction layers provided by a cloud computing environment, in accordance with an embodiment of the present invention.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 includes hardware and software components. Examples of hardware components include: mainframes 961; RISC (Reduced Instruction Set Computer) architecture based servers 962; servers 963; blade servers 964; storage devices 965; and networks and networking components 966. In some embodiments, software components include network application server software 967 and database software 968.

Virtualization layer 970 provides an abstraction layer from which the following examples of virtual entities may be provided: virtual servers 971; virtual storage 972; virtual networks 973, including virtual private networks; virtual applications and operating systems 974; and virtual clients 875.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Examples of workloads and functions which may be provided from this layer include: mapping and navigation 991; software development and lifecycle management 992; virtual classroom education delivery 993; data analytics processing 994; transaction processing 995; and prediction model for determining whether a feature vector of data in each of multiple input sequences should be added to that of the other data in the sequence 996.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for creating a prediction model that predicts chemical properties of a compound from sequence data as a set of feature vectors describing the compound, the sequence data comprising multiple data sequences, the computer-implemented method comprising:

generating, by a hardware processor, a probabilistic prediction model y* predicting an objective variable y in a sequence-to-sequence feature vector copying process determining whether a respective feature vector of the sequence data in multiple input data sequences is added to sequence data in other input data sequences using sparse Bayesian criterion with Automatic Relevance Determination (ARD) and variational approximation;

configuring, by the hardware processor, the probabilistic prediction model y* to (i) assign a prediction function of multiple prediction functions for each of the feature vectors extracted from the sequence data, (ii) identify a relationship between a t-th vector in an i-th data and the objective variable y, and (iii) identify similarities of relationships between the feature vectors and the objective variable y by learning parameters for the similarities that include a strength of co-occurrence of the prediction function in the t-th vector and a t-1-th vector using the sequence data;

identifying, by the hardware processor using the probabilistic prediction model y*, a sequence length which is variable between the multiple data sequences;

predicting, by the hardware processor, the objective variable y as a chemical property of the compound based on the probabilistic prediction model y*; and forming, by a manufacturing system coupled to the hardware processor, a new compound based on the prediction of the objective variable y as a constituent element of the new compound.

2. The computer-implemented method of claim 1, wherein the probabilistic prediction model y* is learned using the sparse Bayesian criterion as follows:

$$y^*(X, Y, \{X_i\}_{i=1}^N) = \mathrm{argmin}_{y^*} \int p(y, X, Y, \{X_i\}_{i=1}^N, \theta)(y^* - y)^2 dy\, dX\, dY\, d\{X_i\}_{i=1}^N d\theta = \int p(y \mid X, Y, \{X_i\}_{i=1}^N) y\, dy$$

where

X is a first set of input sequences in training data, $$Y = \{y_i\}_{i=1}^N$$

is the set of objective variables in the training data, $$\{X_i\}_{i=1}^N$$

is a second set of input sequences in the training data, and θ is a set of parameters to be learned.

3. The computer-implemented method of claim 2, wherein the probabilistic prediction model is as follows:

$$p(y \mid X, \{w_d\}_{d=0}^D, \beta, \{\eta_t\}_{t=0}^T) = \mathrm{Gauss}\left(y \,\middle|\, \sum_d \sum_t w_d \eta_{t,d} x_t,\ 1/\beta\right)$$

$$p(x_t \mid \{w_d\}_{d=0}^D, \{\xi_d\}_{d=0}^D, \eta_t) = \sum_d \mathrm{Gauss}(x_t \mid u_d, 1/\xi_d)^{\eta_{t,d}}$$

$$p(\eta_t \mid \eta_{t-1}, k_{t,t-1}, \lambda_{t,d}) = \exp\left(-k_{t,t-1}(1 - \eta_t^T \eta_{t-1}) - \sum_d \lambda_{t,d}(1 - \eta_{t,d})\right)$$

p(w)=Automatic Relevance Determination (ARD) prior in Bayesian sparse learning, and p(β, ξ, κ, λ)→independent Gamma distributions to restrict the set of parameters to be learned to positive values, where X is the first set of input sequences in the training data, y is an objective variable in the training data, $$\{X_i\}_{i=1}^N$$

is the second set of input sequences in the training data, and t denotes the t-th vector, η denotes a binary variable representing assigning a d-th function to the t-th vector in the i-th data, and w, β, μ, ξ, κ, and λ are parameters to be learned.

4. The computer-implemented method of claim 1, repeating the computer-implemented method to predict another objective variable y' as another property of the compound relative to a different prediction function than that used to predict the objective variable y.

5. The computer-implemented method of claim 1, wherein the probabilistic prediction model is a Gaussian model.

6. The computer-implemented method of claim 1, further comprising replacing a mixture component of the probabilistic prediction model y* with one or more neural networks.

7. The computer-implemented method of claim 1, further comprising assigning a prediction function by an estimation of a hidden variable that explicitly represents an assignation of the prediction function from among a plurality of available prediction functions.

8. The computer-implemented method of claim 7, further comprising predicting based on calculating a summation of outputs of the assigned prediction function of the plurality of available prediction functions.

9. The computer-implemented method of claim 7, wherein the estimation represents roles of each of the feature vectors in each i-th data.

10. The computer-implemented method of claim 1, wherein a hidden variable is provided in a form of $\eta_{i,t,d}$, where $\eta_i$ is a binary variable representing the assignation of a d-th function to the t-th vector in the i-th data such that $\Sigma_d \eta_{i,t,d}=1$.

11. The computer-implemented method of claim 1, further comprising discarding a predicted object on a basis of contamination of the predicted object, responsive to the prediction of the objective variable involving an element unexpected as a part of the predicted object.

12. The computer-implemented method of claim 1, further comprising altering the new compound to provide a corrected amount of the constituent element based on a determination that the new compound includes an insufficient amount of the constituent element.

13. A computer program product for predicting properties of an object from sequence data as a set of feature vectors describing the object, the computer program product comprising a non-transitory computer readable storage medium having program instructions embodied therewith, the program instructions executable by a computer to cause the computer to perform a method comprising:

generating, by a hardware processor, a probabilistic prediction model y* predicting an objective variable y in a sequence-to-sequence feature vector copying process determining whether a respective feature vector of the sequence data in multiple input data sequences is added to sequence data in other input data sequences using sparse Bayesian criterion with Automatic Relevance Determination (ARD) and variational approximation;

configuring, by the hardware processor, the probabilistic prediction model y* to (i) assign a prediction function of multiple prediction functions for each of the feature vectors extracted from the sequence data, (ii) identify a relationship between a t-th feature vector in an i-th data and the objective variable y, and (iii) identify similarities of relationships between the feature vectors and the objective variable y by learning parameters for the similarities that include a strength of co-occurrence of the prediction function in the t-th vector and a t-1-th vector using the sequence data;

identifying, by the hardware processor using the probabilistic prediction model y*, a sequence length which is variable between the multiple input data sequences;

predicting, by the hardware processor, the objective variable y as a chemical property of the object based on the probabilistic prediction model y*; and forming, by a manufacturing system coupled to the hardware processor, a new compound based on the prediction of the objective variable y as a constituent element of the new compound.

14. The computer program product of claim 13, wherein the probabilistic prediction model y* is learned using the sparse Bayesian criterion as follows:

$$y^*(X, Y, \{X_i\}_{i=1}^N) = \mathrm{argmin}_{y^*} \int p(y, X, Y, \{X_i\}_{i=1}^N, \theta)(y^* - y)^2 dy\, dX\, dY\, d\{X_i\}_{i=1}^N d\theta = \int p(y \mid X, Y, \{X_i\}_{i=1}^N) y\, dy$$

where

X is a first set of input sequences in training data, $$Y = \{y_i\}_{i=1}^N$$

is a set of objective variables in the training data, $$\{X_i\}_{i=1}^N$$

is a second set of input sequences in the training data, and

θ is a set of parameters to be learned.

15. The computer program product of claim 14, wherein the probabilistic prediction model is as follows:

$$p(y \mid X, \{w_d\}_{d=0}^D, \beta, \{\eta_t\}_{t=0}^T) = \mathrm{Gauss}\left(y \mid \sum_d \sum_t w_d \eta_{t,d} x_t, 1/\beta\right)$$

$$p(x_t \mid \{w_d\}_{d=0}^D, \{\xi_d\}_{d=0}^D, \eta_t) = \sum_d \mathrm{Gauss}(x_t \mid u_d, 1/\xi_d)^{\eta_{t,d}}$$

$$p(\eta_t \mid \eta_{t-1}, k_{t,t-1}, \lambda_{t,d}) = \exp\left(-k_{t,t-1}(1 - \eta_t^T \eta_{t-1}) - \sum_d \lambda_{t,d}(1 - \eta_{t,d})\right)$$

p(w)=Automatic Relevance Determination (ARD) prior in Bayesian sparse learning, and p(β, ξ, κ, λ)→independent Gamma distributions to restrict the set of parameters to be learned to positive values, where X is the first set of input sequences in training data, y is an objective variable in the training data, t denotes the t-th feature vector, η denotes a binary variable representing assigning a d-th function to the t-th vector in the i-th data, and w, β, μ, ξ, k, and λ are parameters to be learned.

16. The computer program product of claim 13, repeating the method to predict another objective variable y' as another property of the data sequence relative to a different prediction function than that used to predict the object variable y.

17. The computer program product of claim 13, wherein the probabilistic prediction model is a Gaussian model.

18. The computer program product of claim 13, further comprising replacing a mixture component of the probabilistic prediction model with one or more neural networks.

19. A computer processing system for predicting properties of an object from sequence data as a set of feature vectors describing the object, the computer processing system comprising:

a memory for storing program code; and a hardware processor for executing the program code to:

generate a probabilistic prediction model y* predicting an objective variable y in a sequence-to-sequence feature vector copying process determining whether a respective feature vector of the sequence data in multiple input data sequences is added to sequence data in other input data sequences using sparse Bayesian criterion with Automatic Relevance Determination (ARD) and variational approximation;

configure the probabilistic prediction model y* to (i) assign a prediction function of multiple prediction functions for each of the feature vectors extracted from the sequence data, (ii) identify a relationship between a t-th feature vector in an i-th data and the objective variable y, and (iii) identify similarities of relationships between the feature vectors and the objective variable y by learning parameters for the similarities that include a strength of co-occurrence of the prediction function in the t-th vector and a t-1-th vector using the sequence data;

identify, using the probabilistic prediction model y*, a sequence length which is variable between the multiple input data sequences;

predict the objective variable y as a chemical property of the object based on the probabilistic prediction model y*; and a manufacturing system coupled to the hardware processor for forming a new compound based on the prediction of the objective variable y as a constituent element of the new compound.

* * * * *